US010602113B2

(12) United States Patent
Amano

(10) Patent No.: US 10,602,113 B2
(45) Date of Patent: Mar. 24, 2020

(54) MEDICAL IMAGING DEVICE AND MEDICAL OBSERVATION SYSTEM

(71) Applicant: Sony Olympus Medical Solutions Inc., Tokyo (JP)

(72) Inventor: Kohtaro Amano, Tokyo (JP)

(73) Assignee: SONY OLYMPUS MEDICAL SOLUTIONS INC., Tokyo (JP)

( * ) Notice: Subject to any disclaimer, the term of this patent is extended or adjusted under 35 U.S.C. 154(b) by 45 days.

(21) Appl. No.: 15/897,176

(22) Filed: Feb. 15, 2018

(65) Prior Publication Data

US 2018/0262736 A1 Sep. 13, 2018

(30) Foreign Application Priority Data

Mar. 13, 2017 (JP) ................................ 2017-047788

(51) Int. Cl.

| | |
|---|---|
| ***H04N 13/111*** | (2018.01) |
| ***A61B 1/00*** | (2006.01) |
| ***A61B 1/04*** | (2006.01) |
| ***H04N 13/239*** | (2018.01) |
| ***H04N 13/296*** | (2018.01) |
| ***H04N 13/254*** | (2018.01) |
| ***A61B 1/06*** | (2006.01) |
| ***A61B 1/005*** | (2006.01) |
| ***H04N 13/106*** | (2018.01) |
| ***A61B 1/002*** | (2006.01) |
| ***H04N 5/225*** | (2006.01) |

(52) U.S. Cl.

CPC ............ *H04N 13/111* (2018.05); *A61B 1/002* (2013.01); *A61B 1/00006* (2013.01); *A61B 1/00009* (2013.01); *A61B 1/0052* (2013.01); *A61B 1/00188* (2013.01); *A61B 1/00193* (2013.01); *A61B 1/042* (2013.01); *A61B 1/0669* (2013.01); *H04N 13/106* (2018.05); *H04N 13/239* (2018.05); *H04N 13/254* (2018.05); *H04N 13/296* (2018.05); *A61B 1/00045* (2013.01); *A61B 1/00195* (2013.01); *H04N 2005/2255* (2013.01)

(58) Field of Classification Search

None

See application file for complete search history.

(56) References Cited

U.S. PATENT DOCUMENTS

2013/0136379 A1 * 5/2013 Zheng ................ H04N 5/23254 382/296

2014/0210945 A1 * 7/2014 Morizumi ............ H04N 13/239 348/45

FOREIGN PATENT DOCUMENTS

JP 6-160731 6/1994

* cited by examiner

*Primary Examiner* — Dakshesh D Parikh

(74) *Attorney, Agent, or Firm* — Xsensus LLP

(57) ABSTRACT

A medical imaging device includes: a left eye imaging element including a left eye light receiving surface configured to receive left eye observation light from an observed region of a subject; and a right eye imaging element including a right eye light receiving surface configured to receive right eye observation light being an observation light from the observed region and having a parallax from the left eye observation light. The left eye imaging element and the right eye imaging element are arranged such that: short sides of the left eye light receiving surface and the right eye light receiving surface are along a direction in which an optical axes of the left eye observation light and the right eye observation light are juxtaposed with each other; and long sides of the left eye light receiving surface and long sides of the right eye light receiving surface oppose each other.

7 Claims, 12 Drawing Sheets

MEDICAL IMAGING DEVICE AND MEDICAL OBSERVATION SYSTEM

CROSS-REFERENCE TO RELATED APPLICATION(S)

The present application claims priority to and incorporates by reference the entire contents of Japanese Patent Application No. 2017-047788 filed in Japan on Mar. 13, 2017.

BACKGROUND

The present disclosure relates to a medical imaging device and a medical observation system.

In the medical field, medical observation systems for capturing images of subjects (inside living bodies) by using imaging elements, and stereoscopically observing inside the living bodies are known (see, for example, Japanese Unexamined Patent Application, Publication No. 06-160731).

A medical observation system (stereoscopic endoscope apparatus) described in Japanese Unexamined Patent Application, Publication No. 06-160731 includes a rigid endoscope and a medical imaging device (TV camera).

The rigid endoscope has a pair of juxtaposed optical systems having the same configuration in a rigid insertion unit thereof, and left and right eye observation lights having a parallax from each other are respectively taken in by the pair of optical systems.

The medical imaging device includes two imaging elements (left and right eye imaging elements), and the left and right eye observation lights taken in by the rigid endoscope are respectively imaged by the two imaging elements.

SUMMARY

Unless specially ordered, imaging elements have rectangular light receiving surfaces. Further, in general, an imaging element is arranged in a posture where a light receiving surface thereof is orthogonal to an optical axis of incident light, a long side direction of the light receiving surface is along a horizontal direction, and a short side direction thereof is along a vertical direction.

In the medical imaging device described in Japanese Unexamined Patent Application, Publication No. 06-160731, when the two imaging elements are arranged in the above described posture, the two imaging elements will be arranged such that longs sides of each of their light receiving surfaces will be along the horizontal direction and their short sides will oppose each other. When the two imaging elements are arranged as described above, the long sides of the light receiving surfaces of the two imaging elements will be lined up in series, and as a result, there will be a problem that the medical imaging device will be increased in size in the horizontal direction and downsizing of the medical imaging device will be hindered.

According to one aspect of the present disclosure, there is provided a medical imaging device including: a left eye imaging element including a left eye light receiving surface configured to receive left eye observation light from an observed region of a subject, the left eye light receiving surface being rectangular, and the left eye imaging element being configured to output a left eye image signal corresponding to the left eye observation light; and a right eye imaging element including a right eye light receiving surface configured to receive right eye observation light being an observation light from the observed region and having a parallax from the left eye observation light, the right eye light receiving surface being rectangular, and the right eye imaging element being configured to output a right eye image signal corresponding to the right eye observation light, wherein the left eye imaging element and the right eye imaging element are arranged such that: each of short sides of the left eye light receiving surface and short sides of the right eye light receiving surface are along a direction in which an optical axis of the left eye observation light and an optical axis of the right eye observation light are juxtaposed with each other; and long sides of the left eye light receiving surface and long sides of the right eye light receiving surface oppose each other.

DETAILED DESCRIPTION

Hereinafter, by reference to the drawings, embodiments will be described. The present disclosure is not limited by the embodiments described below. Further, the same portions will be assigned with the same reference signs, throughout the drawings.

First Embodiment

Schematic Configuration of Medical Observation System

Figure 1:
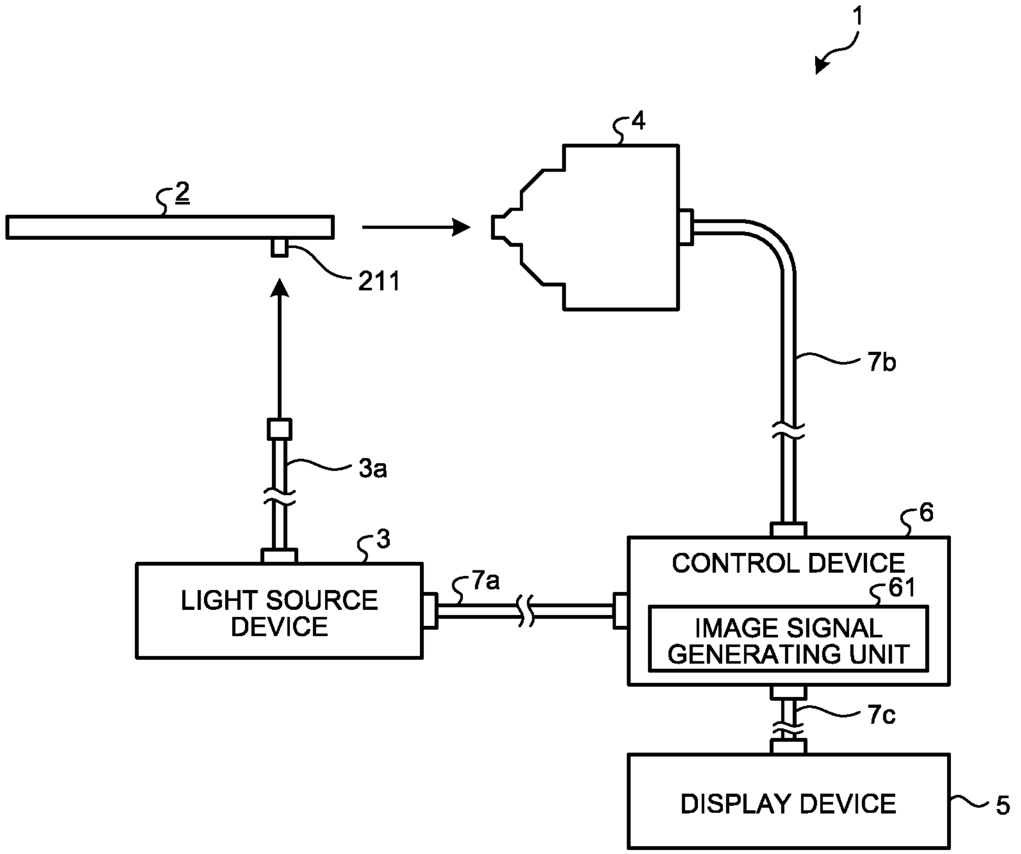
FIG. 1 is a diagram depicting a schematic configuration of a medical observation system according to a first embodiment.

FIG. 1 is a diagram depicting a schematic configuration of a medical observation system 1 according to a first embodiment.

The medical observation system 1 is a system that is used in the medical field, and that is for stereoscopic observation of inside of a living body. This medical observation system 1 includes, as depicted in FIG. 1, a scope 2, a light source device 3, a light guide cable 3*a*, an endoscope camera head 4, a display device 5, a control device 6, and first to third transmission cables 7*a* to 7*c*.

The scope 2 is a rigid endoscope inserted into a living body. In the first embodiment, the scope 2: is formed of a twin lens relay type scope; takes in each of left and right eye observation lights from an observed region in a living body, the left and right eye observation lights having a parallax from each other; and emits the left and right eye observation lights therefrom.

A detailed configuration of the scope 2 will be described later.

One end of the light guide cable 3*a* is connected to the light source device 3, which supplies light for illuminating inside a living body, to the one end of the light guide cable 3*a*, under control by the control device 6.

The one end of the light guide cable 3*a* is connected to the light source device 3, and the other end thereof is connected to the scope 2. The light guide cable 3*a* supplies the light supplied from the light source device 3, to the scope 2.

The endoscope camera head 4 has functions as a medical imaging device according to the present disclosure. This endoscope camera head 4 is a portion that is: attachably and detachably connected to the scope 2; inserted in the scope 2; and held by a doctor or the like when used by the doctor or the like. The endoscope camera head 4 generates a left eye image signal by imaging the left eye observation light emitted from the scope 2, and generates a right eye image signal by imaging the right eye observation light emitted from the scope 2.

A detailed configuration of the endoscope camera head 4 will be described later.

The display device 5 is configured, for example, by use of a 3D display of the integral imaging type, the multiple lens type, or the like, and displays thereon a three dimensional image (stereoscopic image) based on a three dimensional image signal processed by the control device 6.

The control device 6 includes a central processing unit (CPU) or the like, and respectively connects to the light source device 3, the endoscope camera head 4, and the display device 5, via the first to third transmission cables 7*a* to 7*c*. The control device 6 comprehensively controls operation of the light source device 3 by outputting control signals to the light source device 3 via the first transmission cable 7*a*. Further, the control device 6 generates the three dimensional image signal by executing various types of image processing on the right and left eye image signals received from the endoscope camera head 4 via the second transmission cable 7*b*, and outputs the three dimensional image signal to the display device 5 via the third transmission cable 7*c*. Furthermore, the control device 6 outputs control signals, synchronization signals, clocks, electric power, and the like, to the endoscope camera head 4, via the second transmission cable 7*b*.

The transmission of the left and right eye image signals to the control device 6 from the endoscope camera head 4 via the second transmission cable 7*b* may be executed by transmission of the left and right eye image signals through optical signals, or transmission thereof through electric signals. The same applies to the transmission of the control signals, the synchronization signals, and the clocks, from the control device 6 to the endoscope camera head 4 via the second transmission cable 7*b*.

The function of generating the three dimensional image signal by executing various types of image processing on the left and right eye image signals (an image signal generating unit 61 (FIG. 1)) in the control device 6 will be described later.

Configuration of Scope

Next, a configuration of the scope 2 will be described.

Figure 2:
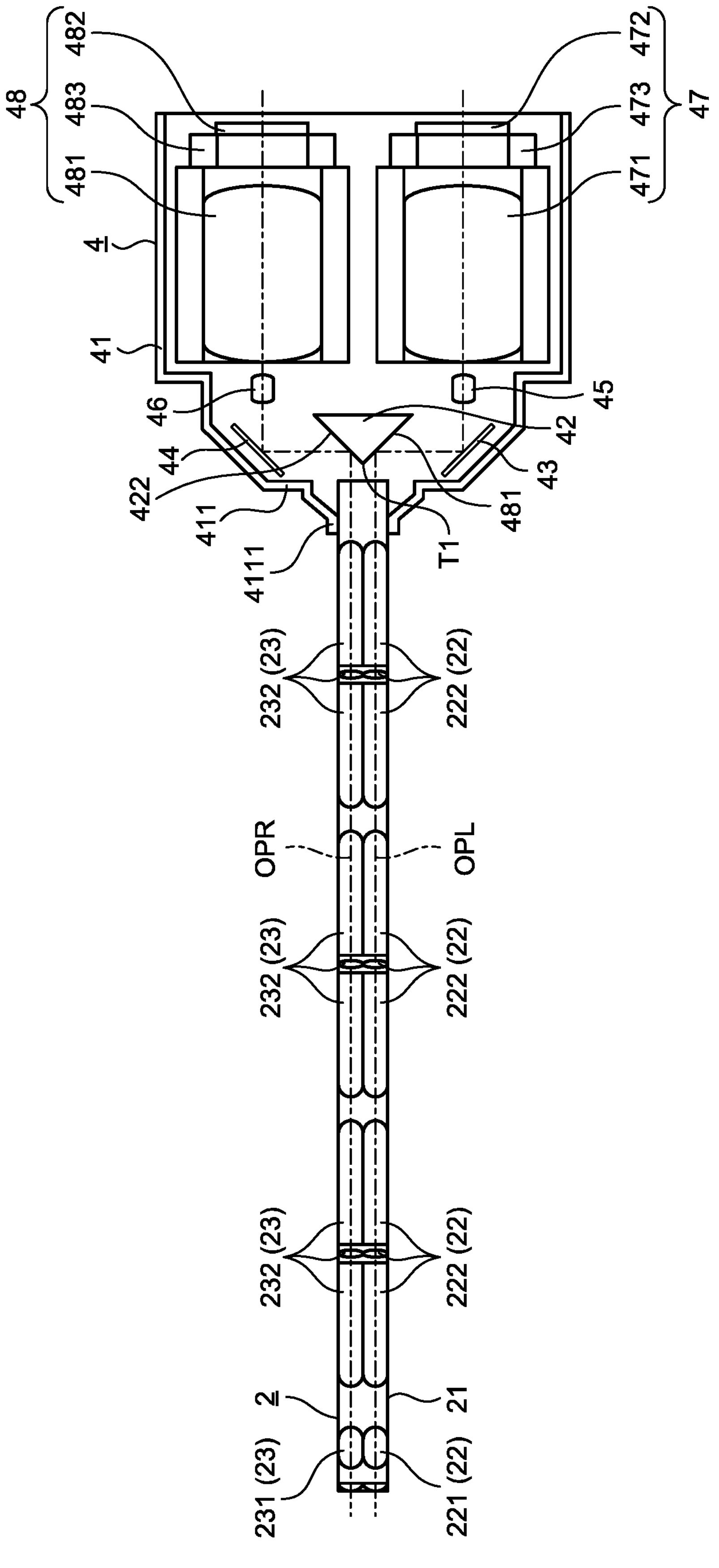
FIG. 2 is a diagram depicting a configuration of a scope and an endoscope camera head.

FIG. 2 is a diagram depicting a configuration of the scope 2 and the endoscope camera head 4.

In FIG. 2, a direction orthogonal to the plane of paper of FIG. 2 corresponds to a vertical direction at the time of use of the scope 2 and the endoscope camera head 4. "Vertical direction" referred to below means the vertical direction at the time of their use (the direction orthogonal to the plane of paper of FIG. 2). Further, "left-right direction" referred to below means a horizontal direction at the time of their use and an up-down direction in FIG. 2.

The scope 2 includes, as depicted in FIG. 2, an insertion tube 21 and left and right eye optical systems 22 and 23.

The insertion tube 21 is rigid, or at least a part thereof is flexible, and the insertion tube 21 has an elongated shape.

Inside this insertion tube 21, left and right eye optical paths OPL and OPR (FIG. 2) have been set, which extend along a central axis of the insertion tube 21, and which are juxtaposed with each other to be symmetrical to each other in the left-right direction (symmetrical in the up-down direction in FIG. 2) about the central axis.

Further, a connector 211 (FIG. 1), which protrudes along a radial direction, and to which the other end of the light guide cable 3*a* is connected, is provided on an outer peripheral surface of the insertion tube 21. In FIG. 2, for convenience of explanation, depiction of the connector 211 has been omitted. Light supplied to the scope 2 from the light source device 3 via the light guide cable 3*a* is emitted from a distal end of the insertion tube 21 (from a left end portion in FIG. 2) via a light guide (not depicted in the drawings) provided inside the insertion tube 21, and inside of a living body is irradiated with the emitted light. Observation lights (left and right eye observation lights) reflected by the observed region in the living body, the observation lights resulting from the irradiation of the inside of the living body, are taken in from the distal end of the insertion tube 21.

The left eye optical system 22 is arranged in the left eye optical path OPL inside the insertion tube 21, and includes, in order from a distal end side thereof, a left eye objective optical system 221 and a left eye relay optical system 222.

The left eye objective optical system 221 is provided at the distal end of the insertion tube 21, and takes in the left eye observation light from the observed region in the living body.

The left eye relay optical system 222 optically guides the left eye observation light taken in by the left eye objective optical system 221, to a proximal end (a right end portion in FIG. 2) of the insertion tube 21. The left eye observation light is then emitted from the proximal end of the insertion tube 21.

The right eye optical system 23 is arranged in the right eye optical path OPR inside the insertion tube 21, and includes, in order from a distal end side thereof, a right eye objective optical system 231 and a right eye relay optical system 232.

The right eye objective optical system 231 is provided at the distal end of the insertion tube 21, and takes in the right eye observation light from the observed region in the living body.

The right eye relay optical system 232 optically guides the right eye observation light taken in by the right eye objective optical system 231, to the proximal end of the insertion tube 21. The right eye observation light is then emitted from the proximal end of the insertion tube 21.

As described above, the left and right eye optical systems 22 and 23 are arranged with a certain interval therebetween in the radial direction inside the insertion tube 21. Therefore, the scope 2 takes in and emits the left and right eye observation lights having a parallax from each other.

Configuration of Endoscope Camera Head

Next, a configuration of the endoscope camera head 4 will be described.

The endoscope camera head 4 includes, as depicted in FIG. 2, a casing 41, a triangular prism 42, left and right eye mirrors 43 and 44, left and right eyepiece optical systems 45 and 46, and left and right eye imaging units 47 and 48.

The casing 41 has an approximately cuboidal shape, and accommodates therein the members 42 to 48.

In this casing 41, on one side surface 411 thereof, an insertion port 4111, which protrudes outward, and into which a proximal end side of the insertion tube 21 is inserted, is formed.

The triangular prism 42 is formed of a triangular prism with a bottom surface having a shape of an isosceles right triangle. Further, inside the casing 41, the triangular prism 42 is arranged in a posture where: the central axis of the insertion tube 21 passes a vertex T1 of the isosceles right triangle forming the bottom surface of the triangular prism 42; and the central axis is orthogonal to the hypotenuse; in a state where the axis of the triangular prism is along the vertical direction and the insertion tube 21 has been inserted in the insertion port 4111.

The triangular prism 42 causes the left eye observation light emitted from the scope 2 to be reflected downward in FIG. 2 by a first side surface 421 forming one side of two sides interposing therebetween the vertex T1 of the isosceles right triangle forming the bottom surface. Furthermore, the triangular prism 42 causes the right eye observation light emitted from the scope to be reflected upward in FIG. 2 by a second side surface 422 forming the other side of those two sides. Accordingly, the left and right eye observation lights respectively advance in directions opposite to each other by 180° (in the left-right direction) via the triangular prism 42.

The left and right eye mirrors 43 and 44 are arranged, inside the casing 41, with a certain interval therebetween, so as to be symmetrical to each other in the left-right direction with reference to the central axis of the insertion tube 21. Further, the left and right eye mirrors 43 and 44 cause the left and right eye observation lights via the triangular prism 42 to be respectively reflected and to respectively advance in a direction parallel to the central axis of the insertion tube 21.

The left and right eyepiece optical systems 45 and 46 are arranged, inside the casing 41, with a certain interval therebetween, so as to be symmetrical to each other in the left-right direction with reference to the central axis of the insertion tube 21. The left and right eyepiece optical systems 45 and 46 respectively emit the left and right eye observation lights via the left and right eye mirrors 43 and 44 in the direction parallel to the central axis of the insertion tube 21.

The left eye imaging unit 47 is arranged, inside the casing 41, at a position opposite to the left eyepiece optical system 45. The left eye imaging unit 47 generates the left eye image signal by imaging the left eye observation light emitted from the left eyepiece optical system 45. This left eye imaging unit 47 includes, as depicted in FIG. 2: a left eye imaging optical system 471; a left eye imaging element 472; and a left eye element frame 473 that supports the left eye imaging element 472 and fixes the left eye imaging element 472 to the left eye imaging optical system 471.

Figure 4:
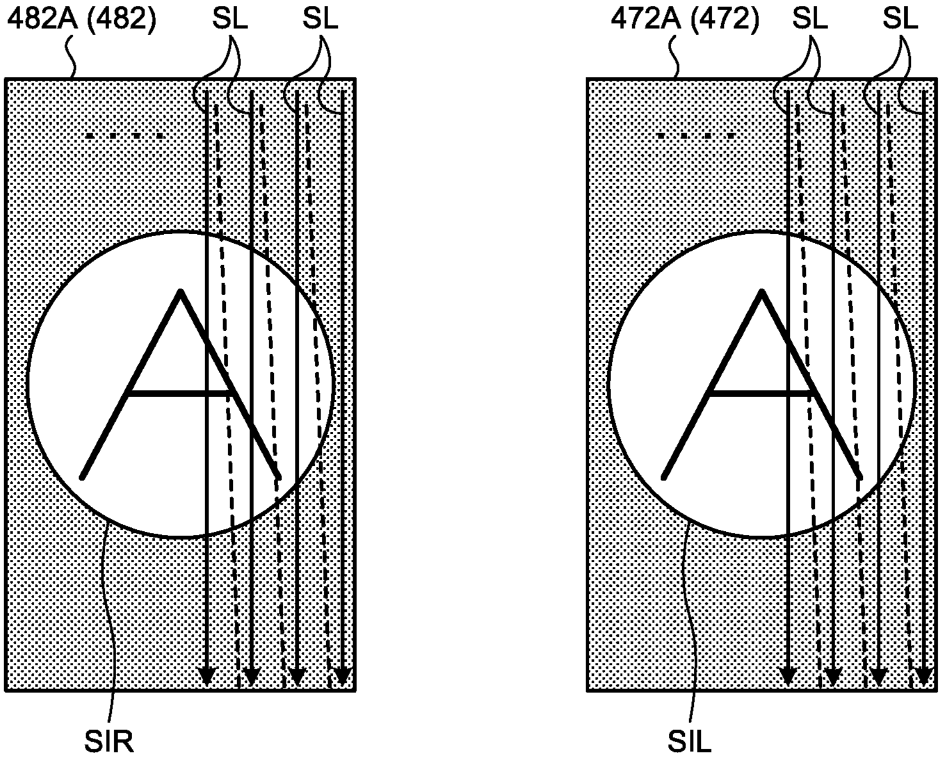
FIG. 4 is a diagram depicting the arrangement posture of the left and right eye imaging elements, and is a diagram depicting a horizontal scanning direction and a vertical scanning direction of the left and right eye imaging elements.

The left eye imaging optical system 471 is configured by use of one or plural lenses movable along the optical axis, and forms an image of left eye observation light having a circular cross section, on a left eye light receiving surface 472A that is in the left eye imaging element 472 and that is rectangular (see FIG. 4).

Provided in this left eye imaging optical system 471 are: an optical zoom mechanism (not depicted in the drawings), which causes the one or plural lenses to move and an angle of view to be changed; and a focus mechanism (not depicted in the drawings), which causes a focal point to be changed. Furthermore, the control device 6 causes the optical zoom mechanism and the focus mechanism to operate and causes the angle of view and the focal point of the left eye imaging optical system 471 to be changed, by outputting control signals to the endoscope camera head 4 via the second transmission cable 7*b*.

The left eye imaging element 472 generates the left eye image signal by imaging the left eye observation light, under control by the control device 6.

This left eye imaging element 472 is configured by use of a sensor chip having: an imaging element (not depicted in the drawings), such as a charge coupled device (CCD) or a complementary metal oxide semiconductor (CMOS), which receives left eye observation light imaged by the left eye imaging optical system 471 and converts the left eye observation light into an electric signal; and a signal processing unit (not depicted in the drawings) that outputs a left eye image signal by executing signal processing (A/D conversion or the like) on the electric signal (analog signal) from the imaging element; the imaging element and the signal processing unit having been formed integrally with each other. The above described signal processing unit may be separately bodied, without being formed integrally with the above described imaging element.

The right eye imaging unit 48 is arranged, inside the casing 41, at a position opposite to the right eyepiece optical system 46. The right eye imaging unit 48 generates a right eye image signal by imaging right eye observation light emitted from the right eyepiece optical system 46. This right eye imaging unit 48 includes, as depicted in FIG. 2: a right eye imaging optical system 481; a right eye imaging element 482; and a right eye element frame 483 that supports the right eye imaging element 482 and fixes the right eye imaging element 482 to the right eye imaging optical system 481.

The right eye imaging optical system 481 has a configuration similar to that of the left eye imaging optical system 471, and forms an image of right eye observation light having a circular cross section, on a right eye light receiving surface 482A that is in the right eye imaging element 482 and that is rectangular (see FIG. 4).

The right eye imaging element 482 has a configuration and a size similar to those of the left eye imaging element 472, and generates a right eye image signal by imaging the right eye observation light, under control by the control device 6.

Arrangement Posture of Left and Right Eye Imaging Elements

Next, an arrangement posture of the left and right eye imaging elements 472 and 482 will be described.

Figure 3:
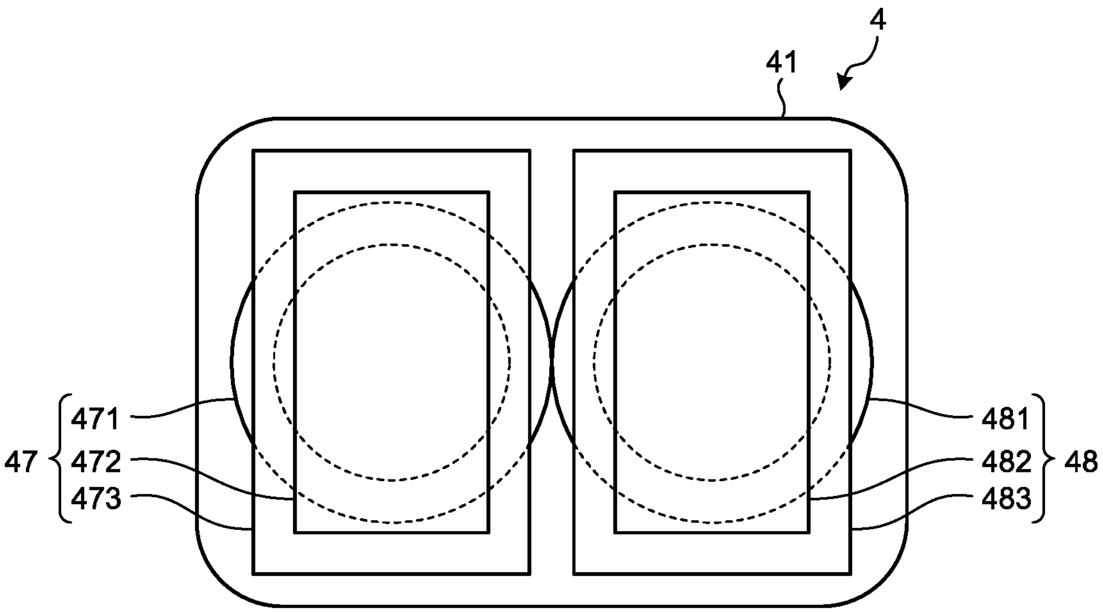
FIG. 3 is a diagram depicting an arrangement posture of left and right eye imaging elements, and is a diagram of inside of the endoscope camera head as viewed from a proximal end side thereof.

FIG. 3 is a diagram depicting the arrangement posture of the left and right eye imaging elements 472 and 482, and is a diagram of inside of the endoscope camera head 4 as viewed from a proximal end side thereof. An up-down direction in FIG. 3 corresponds to the vertical direction at the time of use of the scope 2 and the endoscope camera head 4. FIG. 4 is a diagram depicting the arrangement posture of the left and right eye imaging elements 472 and 482, and is a diagram depicting a horizontal scanning direction and a vertical scanning direction of the left and right eye imaging elements 472 and 482. In FIG. 4, for convenience of explanation, only the left and right eye light receiving surfaces 472A and 482A of the left and right eye imaging elements 472 and 482 are depicted. Further, in FIG. 4, as left and right eye observation lights (subject images) SIL and SIR, for convenience of explanation, the character, "A", is depicted.

The left and right eye imaging elements 472 and 482 are arranged: so as to be in a posture where the left and right eye light receiving surfaces 472A and 482A are respectively orthogonal to the optical axes of the left and right eye observation lights SIL and SIR; and such that the left and right eye light receiving surfaces 472A and 482A are positioned on the same plane. Further, the left and right eye imaging elements 472 and 482 are arranged, as depicted in FIG. 3 or FIG. 4, in a posture where: short sides of the left and right eye light receiving surfaces 472A and 482A are respectively along the left-right direction, in which the optical axes of the left and right eye observation lights SIL and SIR are respectively lined (a direction, in which the left and right eye optical paths OPL and OPR are juxtaposed); and long sides thereof oppose each other.

Further, each of scanning lines SL (arrows indicated with solid lines in FIG. 4) of the left and right eye imaging elements 472 and 482 is set to be along a long side direction of the left and right eye light receiving surfaces 472A and 482A.

Furthermore, the left and right eye imaging elements 472 and 482 are arranged such that their horizontal scanning directions are in the same direction (downward in the example of FIG. 4), and their vertical scanning directions are also in the same direction (leftward in the example of FIG. 4).

Specifically, in the left eye imaging element 472, pixels (not depicted in the drawings) are arranged in a matrix. Further, as indicated with arrows and broken lines in FIG. 4, for pixels of a first line (an arrow at the rightmost end in FIG. 4), the left eye imaging element 472 outputs a left eye image signal from each of the pixels, sequentially from a pixel arranged in a first column (at the uppermost end in FIG. 4) to a pixel arranged in the last column (at the lowermost end in FIG. 4). Subsequently, for pixels of a second row (a second arrow from a right end in FIG. 4), the left eye imaging element 472 outputs a left eye image signal from each of the pixels, sequentially from a pixel arranged in the first column to a pixel arranged in the last column. The left eye imaging element 472 outputs left eye image signals corresponding to one frame by continuing the above processing up to the last line. For output of left eye image signals of the next frame, the left eye imaging element 472 returns to pixels of a first line thereof and executes processing similar to that described above. The right eye imaging element 482 executes similar processing.

Functions of Image Signal Generating Unit

Next, functions of the image signal generating unit 61 will be described.

Hereinafter, among the functions of the image signal generating unit 61, rotation correction executed on left and right eye image signals will be described mainly.

Figure 5:
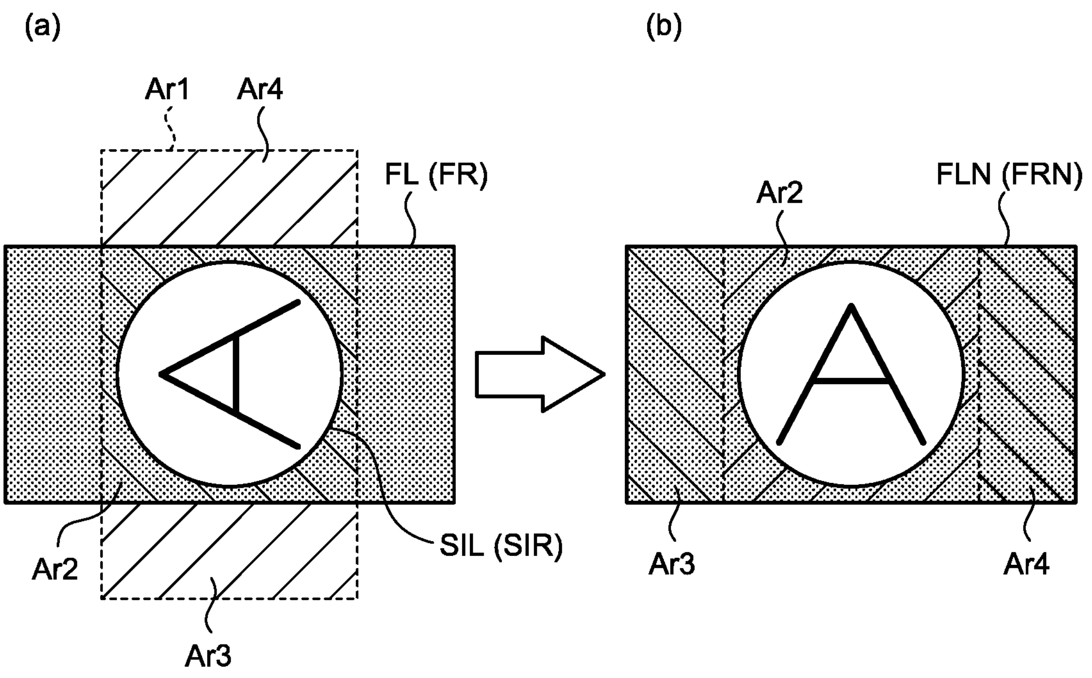
FIG. 5 is a diagram for explanation of rotation correction by an image signal generating unit.

FIG. 5 is a diagram for explanation of the rotation correction by the image signal generating unit 61. A left-right direction in FIG. 5 corresponds to a transverse direction (horizontal direction) of a screen of the display device 5.

As described above, the left and right eye imaging elements 472 and 482 are respectively arranged in a posture where the long sides of the left and right eye light receiving surfaces 472A and 482A are along the vertical direction. Further, the scanning lines SL of the left and right eye imaging elements 472 and 482 are set to be respectively along the long sides of the left and right eye light receiving surfaces 472A and 482A. Therefore, when a left eye image FL based on a left eye image signal or a right eye image FR based on a right eye image signal is displayed as-is, the left or right eye image FL or FR will be displayed, as depicted in the part (a) of FIG. 5, in a state where an up-down direction of the left or right eye observation light SIL or SIR is along the transverse direction of the screen of the display device 5.

Thus, the image signal generating unit 61 executes, as described below, rotation correction on the left or right eye image signal such that display is executed in a state where the up-down direction of the left or right eye observation light SIL or SIR is along a lengthwise direction (vertical direction) of the screen of the display device 5.

The same rotation correction is executed on the left and right eye image signals. Therefore, hereinafter, only the rotation correction executed on the left eye image signal will be described.

An area Ar1, which is indicated with a broken line in a part (a) of FIG. 5 and is rectangular, is an area resulting from rotation of an area having the same aspect ratio as the screen of the display device 5 by 90°.

The image signal generating unit 61 cuts out, from the left eye image FL, an area Ar2 (the part (a) of FIG. 5) included in the area Ar1 of the left eye image FL when the area Ar1 is arranged such that the left eye observation light SIL is positioned at the center of the area Ar1. Further, as depicted in a part (b) of FIG. 5, the image signal generating unit 61 rotates the area Ar2 cut out by 90°, such that the up-down direction of the left eye observation light SIL is along an up-down direction of the screen of the display device 5. Furthermore, as depicted in the part (b) of FIG. 5, the image signal generating unit 61 adds black level areas Ar3 and Ar4 to the area Ar2 that has been rotated, and generates a left eye image FLN having the same aspect ratio as the screen of the display device 5.

Based on left and right eye images FLN and FRN generated as described above, the image signal generating unit 61 generates a three dimensional image signal.

The addition of the black level areas Ar3 and Ar4 to the area Ar2 may be executed before the area Ar2 is rotated by 90°. Further, when a three dimensional image signal is generated by enlargement of parts of the left and right eye observation lights SIL and SIR in the left and right eye images FL and FR, the above described addition of the black level areas Ar3 and Ar4 is unnecessary.

The above described endoscope camera head 4 according to the first embodiment provides the following effects.

Figure 6:
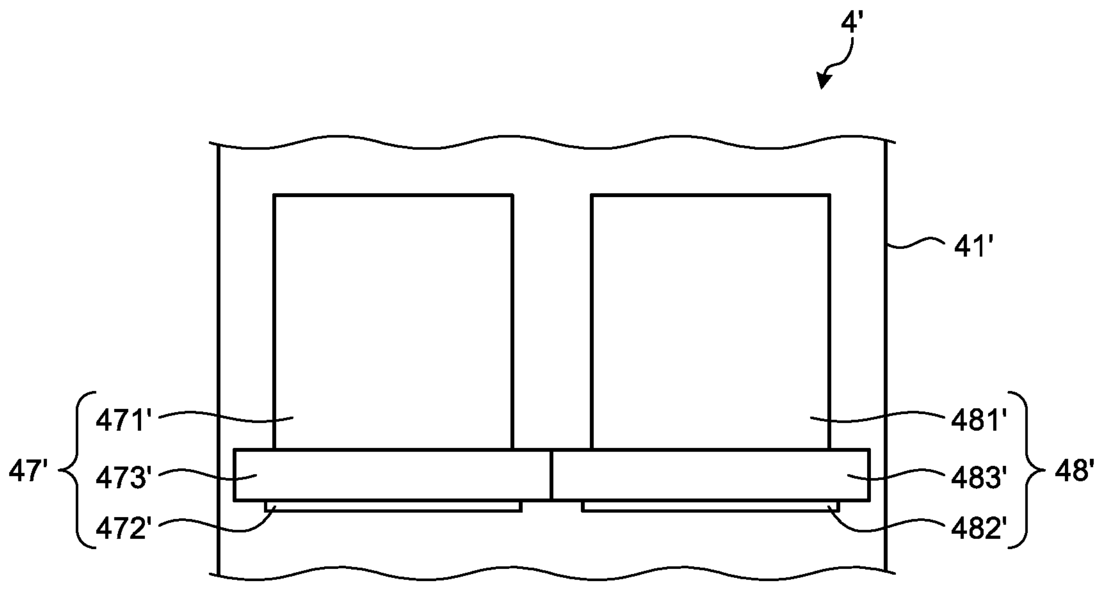
FIG. 6 is a diagram for explanation of effects of the first embodiment.
Figure 7:
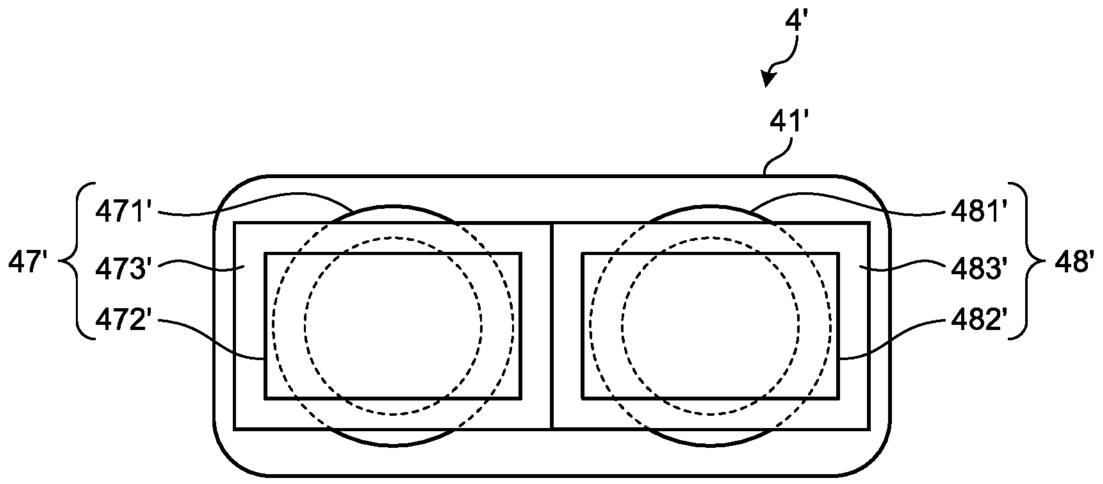
FIG. 7 is a diagram for explanation of the effects of the first embodiment.
Figure 8:
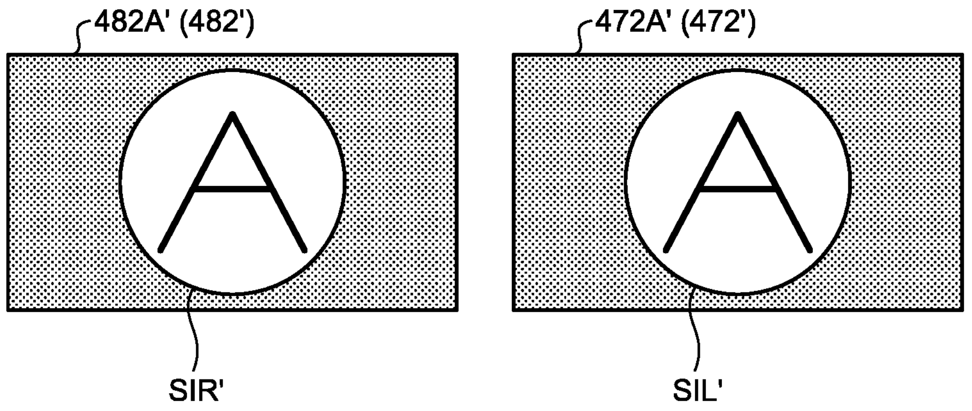
FIG. 8 is a diagram for explanation of the effects of the first embodiment.

FIG. 6 to FIG. 8 are diagrams for explanation of effects of the first embodiment. Specifically, FIG. 6 to FIG. 8 depict an endoscope camera head 4', which has an arrangement posture different from that of the left and right eye imaging elements 472 and 482 according to the first embodiment. In FIG. 6 to FIG. 8, for distinguishment from the endoscope camera head 4 according to the first embodiment, reference signs used for members corresponding to those of the endoscope camera head 4 are added with "'". Further, FIG. 6 is a diagram of left and right eye imaging units 47' and 48' arranged in the endoscope camera head 4' as viewed from thereabove. A left-right direction in FIG. 6 corresponds to the up-down direction in FIG. 2, which is a horizontal direction at the time of use of the endoscope camera head 4'. FIG. 7 is a diagram corresponding to FIG. 3, and is a diagram of inside of the endoscope camera head 4' as viewed from a proximal end side thereof. FIG. 8 is a diagram depicting an arrangement posture of left and right eye imaging elements 472' and 482'. In FIG. 8, for convenience of explanation, only the left and right eye light receiving surfaces 472A' and 482A' of the left and right eye imaging elements 472' and 482' are depicted. Furthermore, in FIG. 8, for convenience of explanation, the character, "A", is depicted as left and right eye observation lights (subject images) SIL' and SIR'.

As depicted in FIG. 6 to FIG. 8, in the endoscope camera head 4', when the left and right eye imaging elements 472' and 482' are arranged such that long sides of each of the left and right eye light receiving surfaces 472A' and 482A' are along the left-right direction and short sides thereof oppose each other, the following problem is caused.

That is, the long sides of the left and right eye light receiving surfaces 472A' and 482A' will be lined up in series, and as a result, size of the endoscope camera head 4' in the left-right direction will be increased, and downsizing of the endoscope camera head 4 will be hindered. In particular, the left and right eye observation lights SIL' and SIR' have circular cross sections. Therefore, on the left and right eye light receiving surfaces 472A' and 482A', both left and right side portions of the left and right eye observation lights SIL' and SIR' are a wasted area (an area shaded with dots in FIG. 8). Furthermore, the endoscope camera head 4' is a portion held by a doctor or the like, and thus when the size of the endoscope camera head 4' in the left-right direction is increased, holdability by the doctor or the like will become very poor.

In contrast, in the endoscope camera head 4 according to the first embodiment, the left and right eye imaging elements 472 and 482 are arranged such that the short sides of each of the left and right eye light receiving surfaces 472A and 482A are along the left-right direction and the long sides thereof oppose each other. In other words, the long sides of the left and right eye light receiving surfaces 472A and 482A in the left and right eye imaging elements 472 and 482 are juxtaposed in parallel with each other in the left-right direction. That is, the wasted area (the area shaded with the dots in FIG. 8) present in both the left and right side portions of the left and right eye observation lights SIL' and SIR' on the left and right eye light receiving surfaces 472A' and 482A' is eliminated.

Therefore, the endoscope camera head 4 according to the first embodiment provides the effect of enabling the size thereof in the left-right direction to be decreased, and enabling downsizing thereof. Further, by the decrease in size in the left-right direction, holdability by a doctor or the like is able to be improved.

Further, in the medical observation system 1 according to the first embodiment, the scanning lines SL of each of the left and right eye imaging elements 472 and 482 are set to be along the long side direction of the left and right eye light receiving surfaces 472A and 482A. The medical observation system 1 includes the image signal generating unit 61 that processes each of the left and right eye image signals, and executes rotation correction of each of the left and right eye images FL and FR.

Therefore, while general imaging elements (imaging elements that are not specially ordered items) are able to be used as the left and right eye imaging elements 472 and 482, the general imaging elements having scanning lines SL that are each along the long side direction of the left and right eye light receiving surfaces 472A and 482A; a three dimensional image, in which the up-down direction of the left and right eye observation lights SIL and SIR is along the lengthwise direction of the screen of the display device 5, is able to be displayed on the display device 5.

Further, in the medical observation system 1 according to the first embodiment, the left and right eye imaging elements 472 and 482 are arranged such that each of their horizontal scanning directions and vertical scanning directions are in the same direction.

Therefore, the same spot on the left and right eye light receiving surfaces 472A and 482A is able to be read at the same timing, and a three dimensional image signal is able to be generated smoothly.

Second Embodiment

Schematic Configuration of Medical Observation System

Figure 9:
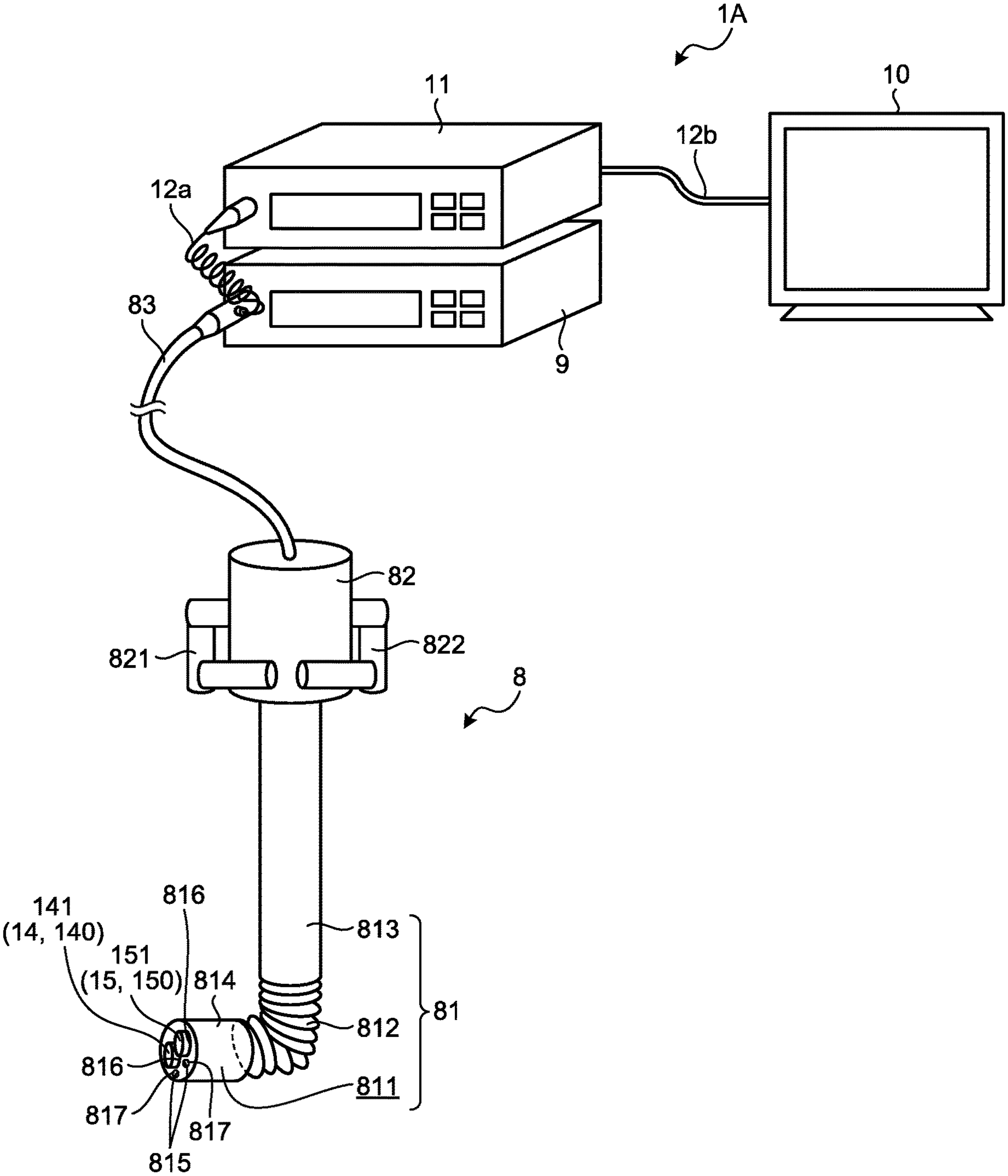
FIG. 9 is a diagram depicting a schematic configuration of a medical observation system according to a second embodiment.

FIG. 9 is a diagram depicting a schematic configuration of a medical observation system 1A according to a second embodiment.

The medical observation system 1A is a system that is used in the medical field, and that is for stereoscopic observation of inside of a living body. This medical observation system 1A includes, as depicted in FIG. 9, a medical endoscope 8, a light source device 9, a display device 10, a control device 11, and fourth and fifth transmission cables 12*a* and 12*b*.

By a scope 81 being inserted into a living body, the medical endoscope 8: takes in left and right eye observation lights from an observed region in the living body, the left and right eye observation lights having a parallax from each other; and outputs left and right eye image signals respectively corresponding to the left and right eye observation lights.

A detailed configuration of the medical endoscope 8 will be described later.

The light source device 9: has a universal cord 83 (FIG. 9) connected thereto, the universal cord 83 composing the medical endoscope 8; and supplies light for illuminating inside the living body, to a light guide (not depicted in the drawings) arranged in the universal cord 83.

The display device 10 is configured, for example, by use of a 3D display of the integral imaging type, the multiple lens type, or the like, and displays thereon a three dimensional image (stereoscopic image) based on a three dimensional image signal processed by the control device 11.

The control device 11 includes a central processing unit (CPU) or the like, and connects to the medical endoscope 8 and the display device 10 respectively via the universal cord 83 and the fourth and fifth transmission cables 12*a* and 12*b*. The control device 11 generates a three dimensional image signal by executing various types of image processing on left and right eye image signals received from the medical endoscope 8 via the fourth transmission cable 12*a* and a signal cable (not depicted in the drawings) arranged in the universal cord 83, and outputs the three dimensional image signal to the display device 10 via the fifth transmission cable 12*b*. Further, the control device 11 outputs control signals, synchronization signals, clocks, electric power, and the like, to the medical endoscope 8, via the fourth transmission cable 12*a* and the above described signal cable.

The transmission of the left and right eye image signals to the control device 11 from the medical endoscope 8 via the fourth transmission cable 12*a* and the above described signal cable may be executed by transmission of the left and right eye image signals through optical signals, or transmission thereof through electric signals. The same applies to the transmission of the control signals, the synchronization signals, and the clocks, from the control device 11 to the medical endoscope 8 via the fourth transmission cable 12*a* and the above described signal cable.

The function of generating a three dimensional image signal by executing various types of image processing on left and right eye image signals in the control device 11 will be described later.

Configuration of Medical Endoscope

Next, a configuration of the medical endoscope 8 will be described.

The medical endoscope 8 includes, as depicted in FIG. 9, a scope 81, an operating unit 82, and the universal cord 83.

Laid inside the scope 81, the operating unit 82, and the universal cord 83 are: a light guide (not depicted in the drawings) that transmits illumination light supplied from the light source device 9, the signal cable (not depicted in the drawings) that transmits left and right eye image signals, and the like.

The scope 81 is a portion that is inserted in a living body, and has functions as an insertion tube.

"Distal end side" referred to below means a distal end side of the scope 81 (a distal end side in an insertion direction into a living body). Further, "proximal end side" referred to below means a side separated from a distal end of the scope 81.

This scope 81 includes, as depicted in FIG. 9, a distal end rigid portion 811 provided at the distal end side, a bent portion 812 connected to a proximal end side of the distal end rigid portion 811, and a proximal end rigid portion 813 connected to a proximal end side of the bent portion 812.

Figure 10A:
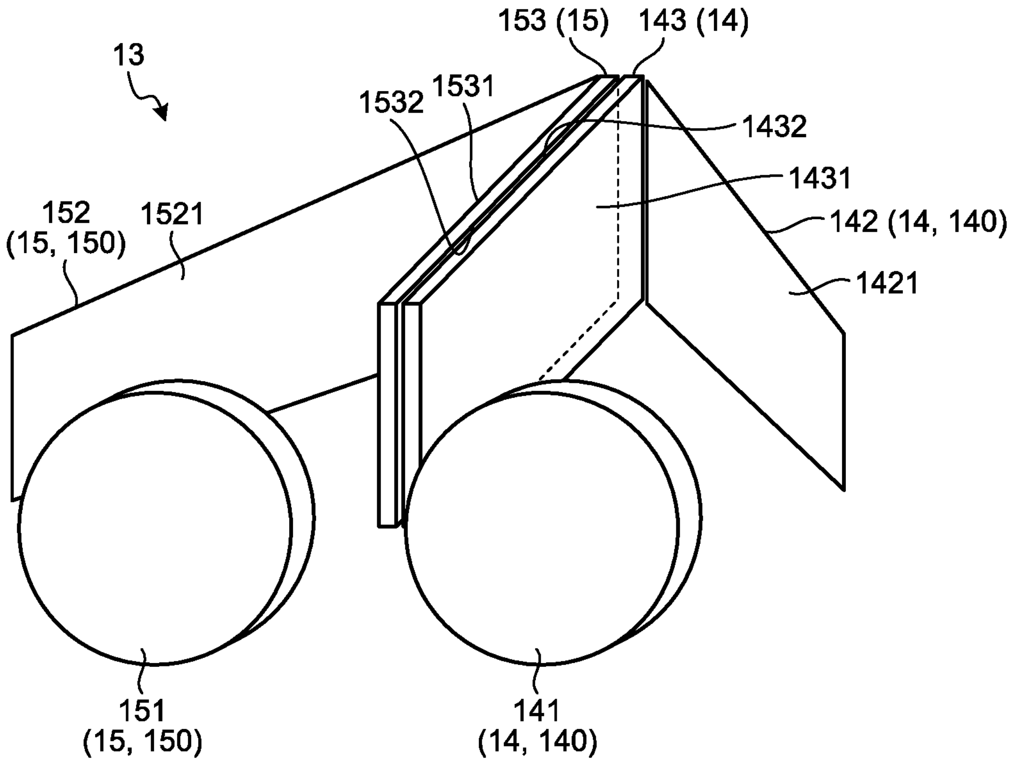
FIG. 10A is a diagram depicting a configuration of a medical imaging device.
Figure 10B:
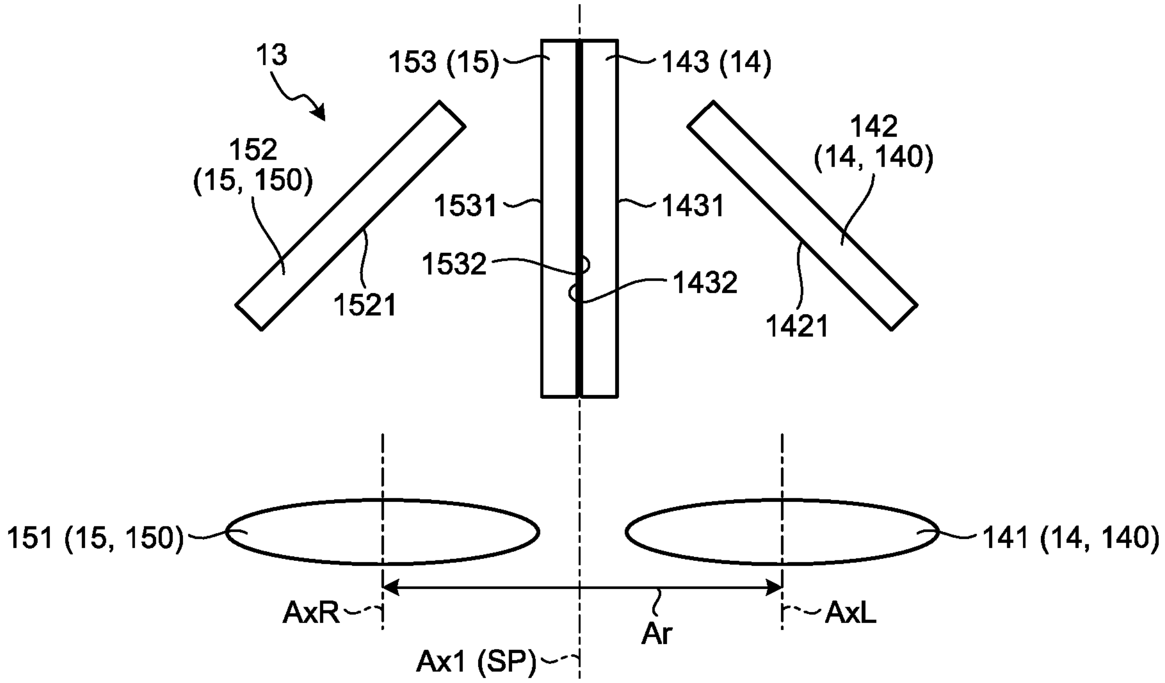
FIG. 10B is a diagram depicting the configuration of the medical imaging device.

The distal end rigid portion 811 includes, as depicted in FIG. 9, a rigid tube 814, and a medical imaging device 13 arranged in the rigid tube 814 (see FIG. 10A and FIG. 10B).

The rigid tube 814 is formed of a hollow body that is elongated and has an annular cross section.

This rigid tube 814 has, as depicted in FIG. 9, a pair of illumination holes 815 and a pair of imaging holes 816 formed therein on an end surface at a distal end side thereof, the pair of illumination holes 815 and the pair of imaging holes 816 making inside and outside of the rigid tube 814 to communicate with each other.

In the pair of illumination holes 815, as depicted in FIG. 9, illumination lenses 817 are respectively arranged. The above described light guide is laid into the rigid tube 814, and is arranged such that an emission end thereof opposes the illumination lenses 817. Inside a living body is illuminated with illumination light emitted from the emission end of the light guide via the illumination lenses 817.

The pair of imaging holes 816 are holes that take in left and right eye observation lights, which result from irradiation of inside of a living body, which have been reflected by an observed region in the living body, and which have a parallax from each other.

FIG. 10A and FIG. 10B are diagrams depicting a configuration of the medical imaging device 13. Specifically, FIG. 10A is a perspective view of the medical imaging device 13 as viewed from a distal end side thereof. FIG. 10B is a diagram of the medical imaging device 13 as viewed from thereabove in FIG. 10A. An up-down direction in FIG. 10A and a direction orthogonal to a plane of paper in FIG. 10B correspond to a vertical direction at the time of use of the medical endoscope 8. Further, "vertical direction" referred to below means the vertical direction at the time of its use. Furthermore, "left-right direction" referred to below means a left-right direction in FIG. 10A and FIG. 10B, which is a horizontal direction at the time of its use. Moreover, "left side" referred to below means a left side (right-side in FIG. 10A and FIG. 10B) as viewed from a proximal end side thereof. In addition, "right side" referred to below means a right side (left side in FIG. 10A and FIG. 10B) as viewed from the proximal end side.

The medical imaging device 13 takes in left and right eye observation lights via the pair of imaging holes 816, and outputs left and right eye image signals respectively corresponding to the left and right eye observation lights. This medical imaging device 13 includes, as depicted in FIG. 10A or FIG. 10B, left and right eye imaging units 14 and 15.

The left eye imaging unit 14 generates a left eye image signal by imaging left eye observation light. This left eye imaging unit 14 includes, as depicted in FIG. 10A or FIG. 10B, a left eye objective lens 141, a left eye mirror 142, and a left eye imaging element 143.

The left eye objective lens 141 is arranged in one imaging hole 716 of the pair of imaging holes 816. The left eye objective lens 141 takes in left eye observation light, which has been reflected by an observed region inside a living body, and which has a circular cross section. That is, the left eye objective lens 141 has functions as a left eye objective optical system.

This left eye objective lens 141 is arranged such that a lens optical axis AxL thereof (FIG. 10B) is parallel to a central axis Ax1 of the rigid tube 814 (FIG. 10B).

In the rigid tube 814, the left eye mirror 142 is arranged to be inclined by approximately 45° with respect to the central axis Ax1, so as to approach an inner surface of the rigid tube 814 toward a distal end side thereof. Further, the left eye mirror 142 has a trapezoidal (isosceles trapezoidal) shape with an inner surface side of the rigid tube 814 being an upper base thereof. A left eye reflecting surface 1421 of the left eye mirror 142 (FIG. 10A and FIG. 10B) reflects left eye observation light advancing parallel to the central axis Ax1 via the left eye objective lens 141, in a direction that is approximately orthogonal to the central axis Ax1, and optically guides the reflected left eye observation light to the left eye imaging element 143. That is, the left eye mirror 142 has functions as a left eye light guide unit.

The left eye objective lens 141 and the left eye mirror 142 have functions as a left eye optical system 140 (FIG. 10A and FIG. 10B).

In the rigid tube 814, the left eye imaging element 143 is arranged in a posture where a left eye light receiving surface 1431 that is rectangular: is parallel to a plane SP, which passes the central axis Ax1 and which is orthogonal to a plane including the central axis Ax1 and the lens optical axis AxL; and opposes the left eye mirror 142. Further, the left eye imaging element 143 is arranged in a posture where long sides of the left eye light receiving surface 1431 are parallel to the central axis Ax1. Under control by the control device 11, the left eye imaging element 143 images left eye observation light via the left eye objective lens 141 and the left eye mirror 142, and generates a left eye image signal. The above described signal cable is laid into the rigid tube 814. The left eye image signal generated by the left eye imaging element 143 is input to the control device 11 via the above described signal cable and fourth transmission cable 12*a*.

This left eye imaging element 143 is configured by use of a sensor chip formed of: an imaging element (not depicted in the drawings), such as a charge coupled device (CCD) or a complementary metal oxide semiconductor (CMOS), which receives left eye observation light and converts the left eye observation light into an electric signal; and a signal processing unit (not depicted in the drawings) that executes signal processing (A/D conversion or the like) on the electric signal (analog signal) from the imaging element and outputs a left eye image signal; the imaging element and the signal processing unit having been formed integrally with each other. The above described signal processing unit may be separately bodied, without being formed integrally with the above described imaging element.

The right eye imaging unit 15 generates a right eye image signal by imaging right eye observation light. This right eye imaging unit 15 includes, as depicted in FIG. 10A or FIG. 10B, a right eye objective lens 151, a right eye mirror 152, and a right eye imaging element 153.

The right eye objective lens 151 is an objective lens having the same shape as the left eye objective lens 141, and is arranged in the other imaging hole 816 of the pair of imaging holes 816, so as to be symmetrical to the left eye objective lens 141 with reference to the plane SP. The right eye objective lens 151 takes in right eye observation light reflected by the observed region in the living body and having a circular cross section. That is, the right eye objective lens 151 has functions as a right eye objective optical system.

The right eye mirror 152 is a mirror having the same shape as the left eye mirror 142, and is arranged to be symmetrical to the left eye mirror 142 with reference to the plane SP, in the rigid tube 814. A right eye reflecting surface 1521 (FIG. 10A and FIG. 10B) of the right eye mirror 152 reflects right eye observation light that advances parallel to the central axis Ax1 via the right eye objective lens 151 in a direction approximately orthogonal to the central axis Ax1, and guides the right eye observation light to the right eye imaging element 153. That is, the right eye mirror 152 has functions as a right eye light guide unit.

The right eye objective lens 151 and the right eye mirror 152 have functions as a right eye optical system 150 (FIG. 10A and FIG. 10B).

The right eye imaging element 153 has the same configuration and shape as the left eye imaging element 143, and is arranged to be symmetrical to the left eye imaging element 143 with reference to the plane SP, in the rigid tube 814. Further, the right eye imaging element 153 has a reverse surface 1532 (FIG. 10A and FIG. 10B) opposite to a right eye light receiving surface 1531 in the right eye imaging element 153, the reverse surface 532 having been stuck on a reverse surface 1432 (FIG. 10A and FIG. 10B) opposite to the left eye light receiving surface 1431 in the left eye imaging element 143. Under control by the control device 11, the right eye imaging element 153 images right eye observation light via the right eye objective lens 151 and the right eye mirror 152, and generates a right eye image signal. The above described signal cable is laid into the rigid tube 814. The right eye image signal generated by the right eye imaging element 153 is input to the control device 11 via the above described signal cable and the fourth transmission cable 12*a*.

As described above, in this second embodiment, the left and right eye imaging units 14 and 15 are arranged symmetrically to each other with reference to the plane SP (a plane orthogonal to an optical axis juxtaposition direction Ar (FIG. 10B), in which the lens optical axes AxL and AxR (FIG. 10B) of the left and right eye objective lenses 141 and 151 are juxtaposed). Further, the left and right eye imaging elements 143 and 153 are arranged such that the left and right eye light receiving surfaces 1431 and 1531 are respectively positioned on planes different from each other and that the reverse surfaces 1432 and 1532 oppose each other in the optical axis juxtaposition direction Ar. More specifically, the left and right eye imaging elements 143 and 153 are arranged such that the left and right eye light receiving surfaces 1431 and 1531 are parallel to each other.

Figure 11:
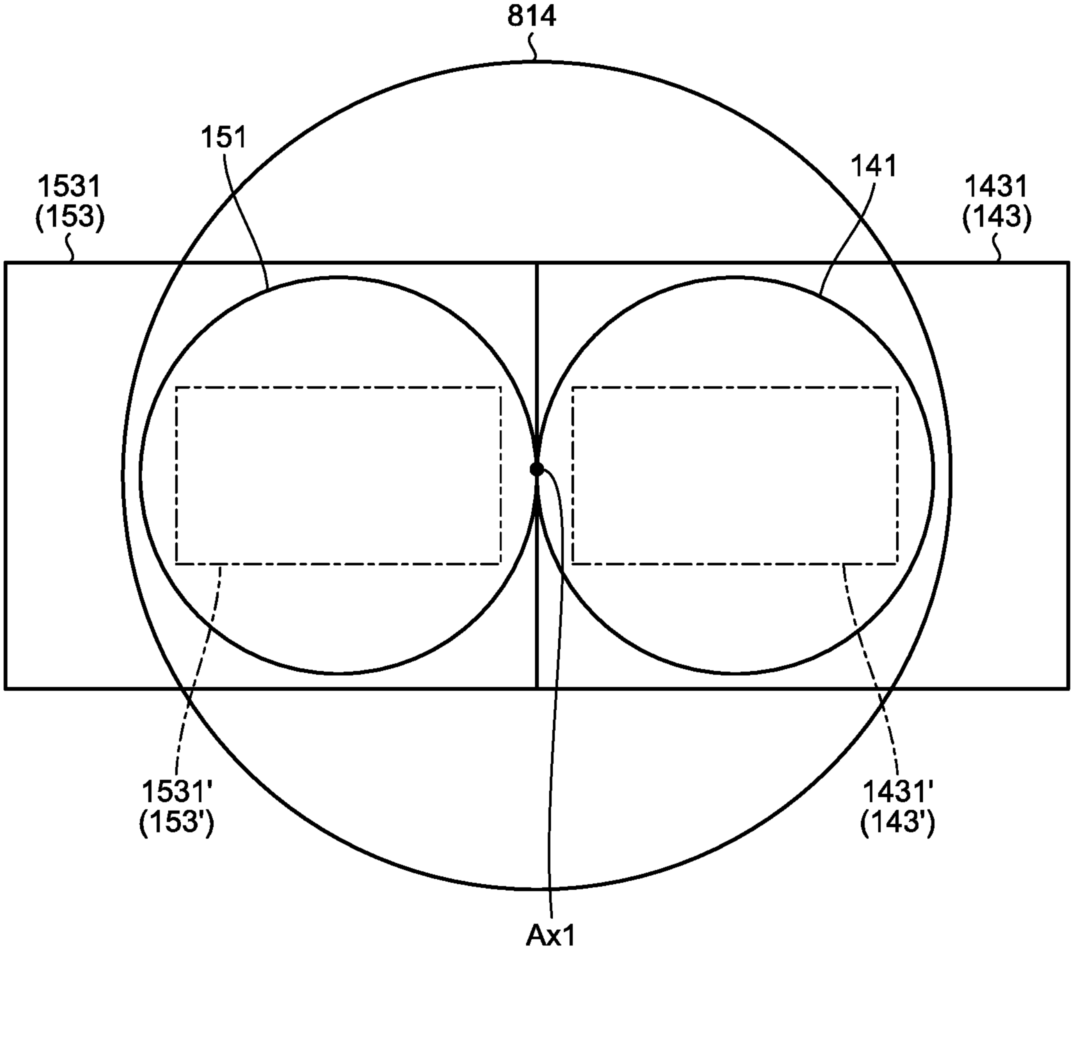
FIG. 11 is a diagram for comparison of sizes (areas) of a rigid tube, left and right eye objective lenses, and left and right eye light receiving surfaces.

FIG. 11 is a diagram for comparison of sizes of the rigid tube 814, the left and right eye objective lenses 141 and 151, and the left and right eye light receiving surfaces 1431 and 1531.

In FIG. 11, the rigid tube 814 and the left and right eye objective lenses 141 and 151 are viewed from a direction along the central axis Ax1. FIG. 11 depicts, for convenience of explanation, a case where the left and right eye light receiving surfaces 1431 and 1531 are arranged such that each of the left and right eye light receiving surfaces 1431 and 1531 is orthogonal to the central axis Ax1.

In this second embodiment, an area of the left eye light receiving surface 1431 is, as depicted in FIG. 11, set to be larger than an area of the left eye objective lens 141. That is, an area of the right eye light receiving surface 1531 is also set to be larger than an area of the right eye objective lens 151.

The bent portion 812 is a portion bendable by plural ring shaped members (not depicted in the drawings) being connected to one another along the central axis Ax1, and connects between the distal end rigid portion 811 and the proximal end rigid portion 813. The bent portion 812 is bent in four directions, upward, downward, leftward, and rightward, according to operation on the operating unit 82 by a doctor or the like. More specifically, by the bent portion 812 being bent upward or downward, an end surface at a distal end side of the distal end rigid portion 811 (the end surface where the illumination holes 815 and the imaging holes 816 are formed) faces, with respect to a central axis Ax2 (see FIG. 12) of the proximal end rigid portion 813, upward (upward along the central axis Ax2 at the time of use of the medical endoscope 8) or downward (downward along the central axis Ax2 at the time of use of the medical endoscope 8). Further, by the bent portion 812 being bent leftward or rightward, the end surface at the distal end side of the distal end rigid portion 811 faces, with respect to the central axis Ax2, leftward (leftward from the central axis Ax2 at the time of use of the medical endoscope 8) or rightward (rightward from the central axis Ax2 at the time of use of the medical endoscope 8).

Figure 12:
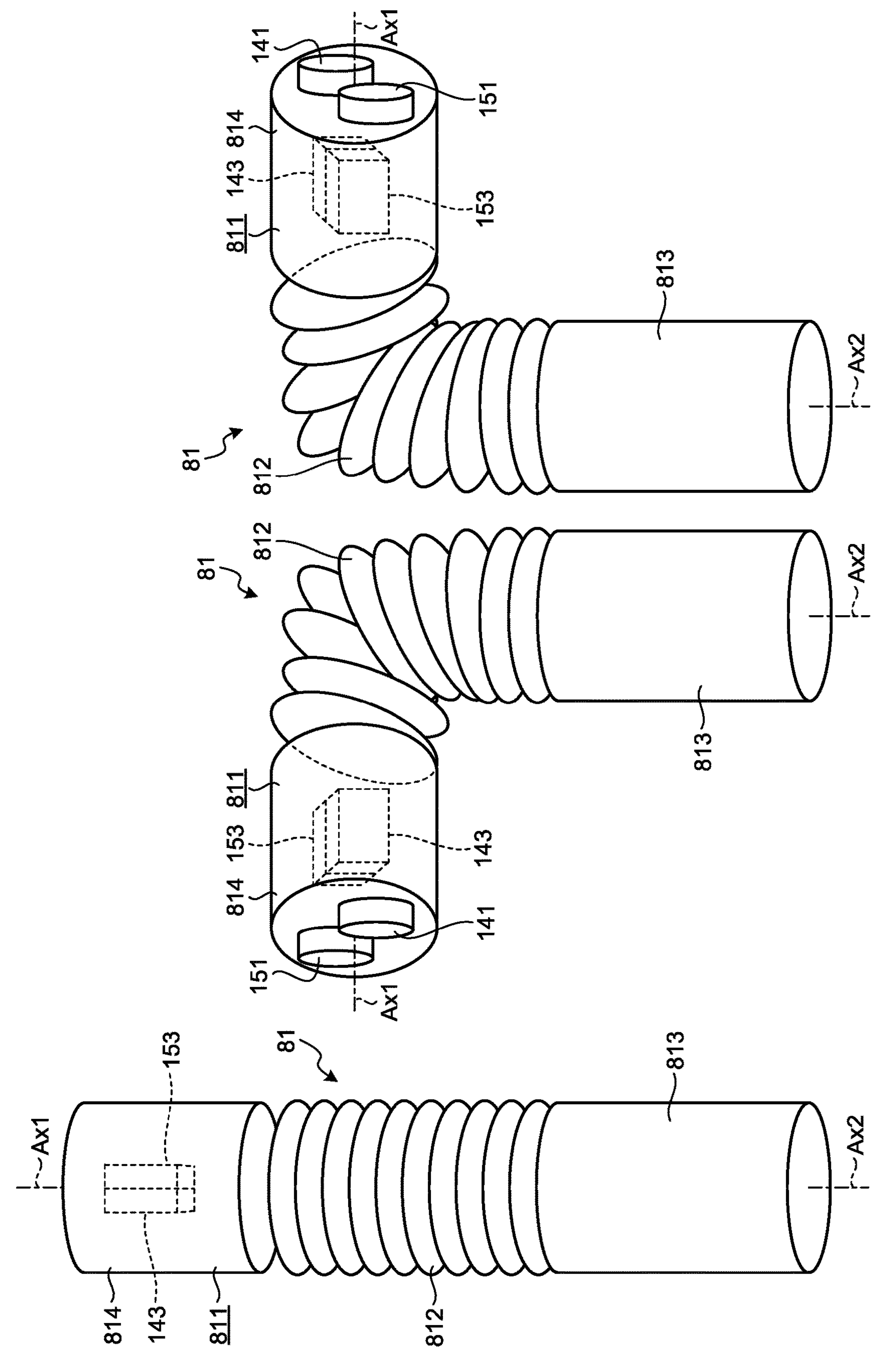
FIG. 12 is a diagram for explanation of functions of a bent portion.

FIG. 12 is a diagram for explanation of functions of the bent portion 812. Specifically, a part (a) of FIG. 12 depicts a state where the bent portion 812 is not bent, the central axes Ax1 and Ax2 are aligned with each other, and the end surface at the distal end side of the distal end rigid portion 811 is made to face forward. A part (b) of FIG. 12 depicts a state where the end surface at the distal end side of the distal end rigid portion 811 is made to face leftward with respect to the central axis Ax2, according to bending of the bent portion 812. A part (c) of FIG. 12 depicts a state where the end surface at the distal end side of the distal end rigid portion 811 is made to face rightward with respect to the central axis Ax2, according bending of the bent portion 812.

As depicted in the parts (a), (b), and (c) of FIG. 12, in any of the state where the bent portion 812 is not bent, and the states where the bent portion 812 is bent leftward and rightward, a short side direction of the left and right eye imaging elements is always in a state of being along the vertical direction. That is, in any of these states, imaging is able to be executed in a state where a top-bottom direction of the left and right eye imaging elements 143 and 153 has been maintained, and an image displayed on a screen of the display device 10 will not be rotated.

The proximal end rigid portion 813 is a rigid tube having an elongated and cylindrical shape, and a length dimension thereof is set to be longer than a length dimension of the rigid tube 814.

The operating unit 82 is a portion that is connected to the proximal end side of the scope 81 (proximal end rigid portion 813), and that receives various operations from a doctor or the like. This operating unit 82 has, as depicted in FIG. 9, two bending operation levers 821 and 822 provided therein for execution of bending operation on the bent portion 812.

One 821 of the bending operation levers draws or releases two wires (not depicted in the drawings) laid in the scope 81 according to operation by a doctor or the like, and causes the bent portion 812 to be bent upward or downward. Further, the other one 822 of the bending operation levers draws or releases other two wires (not depicted in the drawings) laid in the scope 81, according to operation by a doctor or the like, and causes the bent portion 812 to be bent leftward or rightward.

The universal cord 83 extends from the operating unit 82, and has the above described light guide, signal cable, and the like arranged inside thereof.

Configuration of Control Device

Next, a configuration of the control device 11 will be described.

Figure 13:
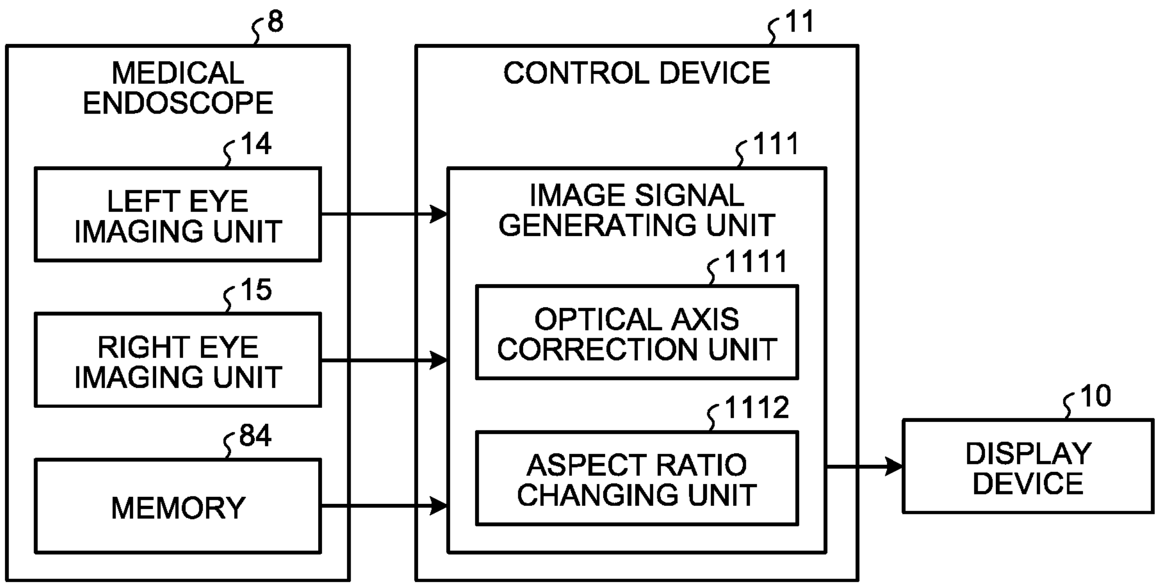
FIG. 13 is a block diagram depicting a configuration of a control device.

FIG. 13 is a block diagram depicting the configuration of the control device 11.

The control device 11 includes, as depicted in FIG. 13, an image signal generating unit 111 that generates a three dimensional image signal by executing various types of image processing on left and right eye image signals.

Hereinafter, among functions of the image signal generating unit 111, mainly an optical axis correction process and an aspect ratio changing process (scaling process) executed on left and right eye image signals will be described.

The image signal generating unit 111 includes, as depicted in FIG. 13, an optical axis correction unit 1111 and an aspect ratio changing unit 1112.

Figure 14:
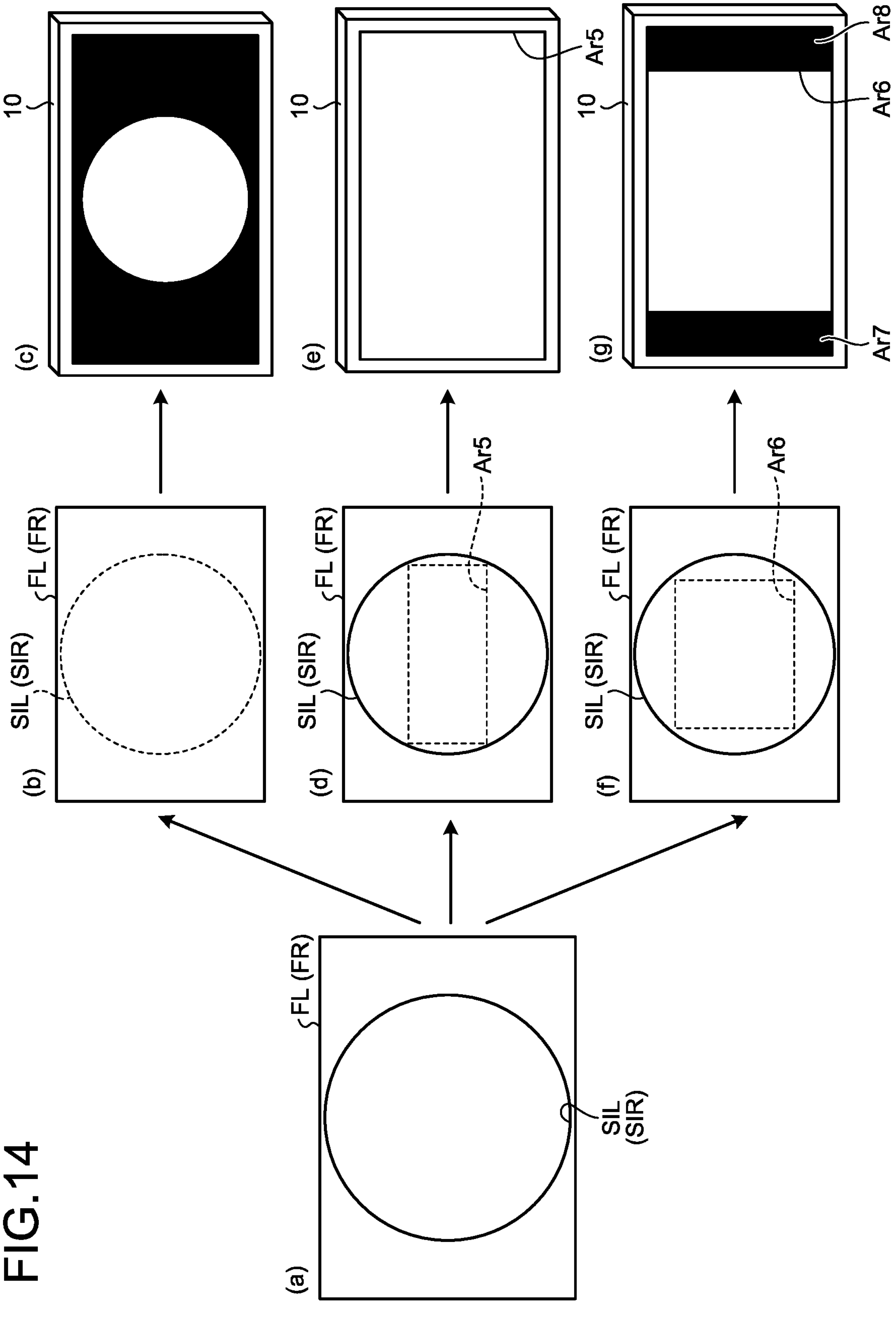
FIG. 14 is a diagram for explanation of an aspect ratio changing process by an aspect ratio changing unit.

FIG. 14 is a diagram for explanation of the aspect ratio changing process by the aspect ratio changing unit 1112. Specifically, a part (a) of FIG. 14 depicts a left eye image FL based on a left eye image signal (a right eye image FR based on a right eye image signal).

As described above, the areas of the left and right eye light receiving surfaces 1431 and 1531 are respectively larger than those of the left and right eye objective lenses 141 and 151. That is, the left and right eye light receiving surfaces 1431 and 1531 respectively capture the entire left and right eye observation lights having the circular cross sections. Therefore, a left eye image FL based on a left eye image signal, and a right eye image FR based on a right eye image signal respectively include, as depicted in the part (a) of FIG. 14, the entire left and right eye observation lights (subject images) SIL and SIR.

The optical axis correction unit 1111 acquires the left and right eye image signals from the medical endoscope 8 (left and right eye imaging units 14 and 15), and acquires optical axis correction data from a memory 84 (FIG. 13) provided in the medical endoscope 8.

The optical axis correction data are correction data specific to the medical endoscope 8, and are data indicating shift amounts of left and right eye observation lights SIL and SIR according to deviation amounts of the lens optical axes AxL and AxR or the like with respect to the left and right eye imaging elements 143 and 153.

Based on the optical axis correction data, in the optical axis correction process on the left and right eye image signals, the optical axis correction unit 1111 respectively shifts the left and right eye images FL and FR (left and right eye observation lights SIL and SIR) by the above described shift amounts.

The aspect ratio changing unit 1112 executes the aspect ratio changing process (scaling process) on the left and right eye images FL and FR that have been subjected to the optical axis correction process by the optical axis correction unit 1111.

For example, when the entire left or right eye observation light SIL or SIR is to be displayed on the screen of the display device 10, as depicted in parts (b) and (c) of FIG. 14, the aspect ratio changing unit 1112 scales the entire left or right eye image FL or FR that has been subjected to the optical axis correction process by the optical axis correction unit 1111.

Further, for example, when a part of the left or right eye observation light SIL or SIR is to be displayed over the entire screen of the display device 10, as depicted in parts (d) and (e) of FIG. 14, the aspect ratio changing unit 1112 cuts out an area Ar5 according to an aspect ratio of the screen of the display device 10 in the left or right eye observation light SIL or SIR from the left or right eye image FL or FR.

Furthermore, for example, when an area Ar6 having an aspect ratio different from that of the screen of the display device 10 in the left or right eye observation light SIL or SIR is to be displayed on the screen, as depicted in parts (f) and (g) of FIG. 14, the aspect ratio changing unit 1112 cuts out the area Ar6 from the left or right eye image FL or FR. The aspect ratio changing unit 1112 then adds black level areas Ar7 and Ar8 (the part (g) of FIG. 14) onto both left and right sides of the area Ar6 such that an image having the same aspect ratio as the screen of the display device 10 is acquired.

Based on the left and right eye images, on which the optical axis correction process and the aspect ratio changing process have been executed as described above, the image signal generating unit 111 generates a three dimensional image signal.

The above described medical imaging device 13 according to the second embodiment provides the following effects.

The medical imaging device 13 according to the second embodiment includes the left and right eye imaging units 14 and 15 that respectively image left and right eye observation lights SIL and SIR from an observed region in a subject, the left and right eye observation lights SIL and SIR having a parallax from each other. The left and right eye imaging units 14 and 15 are arranged symmetrically to each other with reference to the plane SP. Further, the left and right eye imaging elements 143 and 153 are arranged such that the left and right eye light receiving surfaces 1431 and 1531 are positioned on planes different from each other and the reverse surfaces 1432 and 1532 oppose each other in the optical axis juxtaposition direction Ar. That is, the left and right eye imaging elements 143 and 153 are arranged such that, in the rigid tube 814, the left and right eye light receiving surfaces 1431 and 1531 intersect a plane orthogonal to the central axis Ax1 of the rigid tube 814. Thus, as depicted in FIG. 11, sizes (areas) of the left and right eye imaging elements 143 and 153 (left and right eye light receiving surfaces 1431 and 1531) will not be limited by a dimension of an inner diameter of the rigid tube 814; and for example, as compared to a case where the left and right eye imaging elements 143' and 153' are arranged such that the left and right eye light receiving surfaces 1431' and 1531' are respectively orthogonal to a direction along the central axis Ax1, the left and right eye imaging elements 143 and 153 that are larger are able to be adopted.

Therefore, the medical imaging device 13 according to the second embodiment provides an effect of enabling improvement of resolution (increase of pixels) of images imaged by the left and right eye imaging elements 143 and 153.

Further, in the medical imaging device 13 according to the second embodiment, the areas of the left and right eye light receiving surfaces 1431 and 1531 are larger than the areas of the left and right eye objective lenses 141 and 151. That is, the left and right eye images FL and FR respectively include the entire left and right eye observation lights SIL and SIR. Therefore, the optical axis correction process is able to be executed in a state where there is no vignetting in the left and right eye observation lights SIL and SIR. Furthermore, according to arbitrarily set aspect ratios, various aspect ratio changing processes are able to be executed (the parts (b) to (g) of FIG. 14).

Further, in the medical imaging device 13 according to this second embodiment, the left and right eye imaging elements 143 and 153 are arranged such that the left and right eye light receiving surfaces 1431 and 1531 are parallel to each other, and the reverse surfaces 1432 and 1532 are stuck to each other.

Therefore, since the left and right eye imaging elements 143 and 153 (left and right eye light receiving surfaces 1431 and 1531) do not mechanically interfere with the rigid tube 814 in a direction parallel to the central axis Ax, the left and right eye imaging elements 143 and 153 (left and right eye light receiving surfaces 1431 and 1531) are able to be formed long in that direction and sizes (areas) thereof are able to be made the largest. Furthermore, the above described signal processing unit is able to be commonized between the left and right eye imaging elements 143 and 153, and thus the structure of the medical imaging device 13 is able to be simplified.

Further, in the medical imaging device 13 according to this second embodiment, the left and right eye imaging elements 143 and 153 are arranged in the posture where the long sides of the left and right eye light receiving surfaces 1431 and 1531 are parallel to the central axis Ax1.

Unless specially ordered, imaging elements have rectangular light receiving surfaces. That is, by the above described arrangement of the left and right eye imaging elements 143 and 153, imaging elements that are general imaging elements (imaging elements that are not specially ordered items) and that are comparatively large are able to be adopted in the medical imaging device 13 according to this second embodiment.

Further, in the medical imaging device 13 according to this second embodiment, each of the left and right eye reflecting surfaces 1421 and 1521 has a trapezoidal shape with an inner surface side of the rigid tube 814 being an upper base thereof.

Therefore, in the rigid tube 814, the left and right eye reflecting surfaces 1421 and 5121 are able to be made as large as possible.

Third Embodiment

Next, a third embodiment will be described.

In the following description, any component similar to that of the above described second embodiment will be assigned with the same reference sign and detailed description thereof will be omitted or simplified.

Figure 15A:
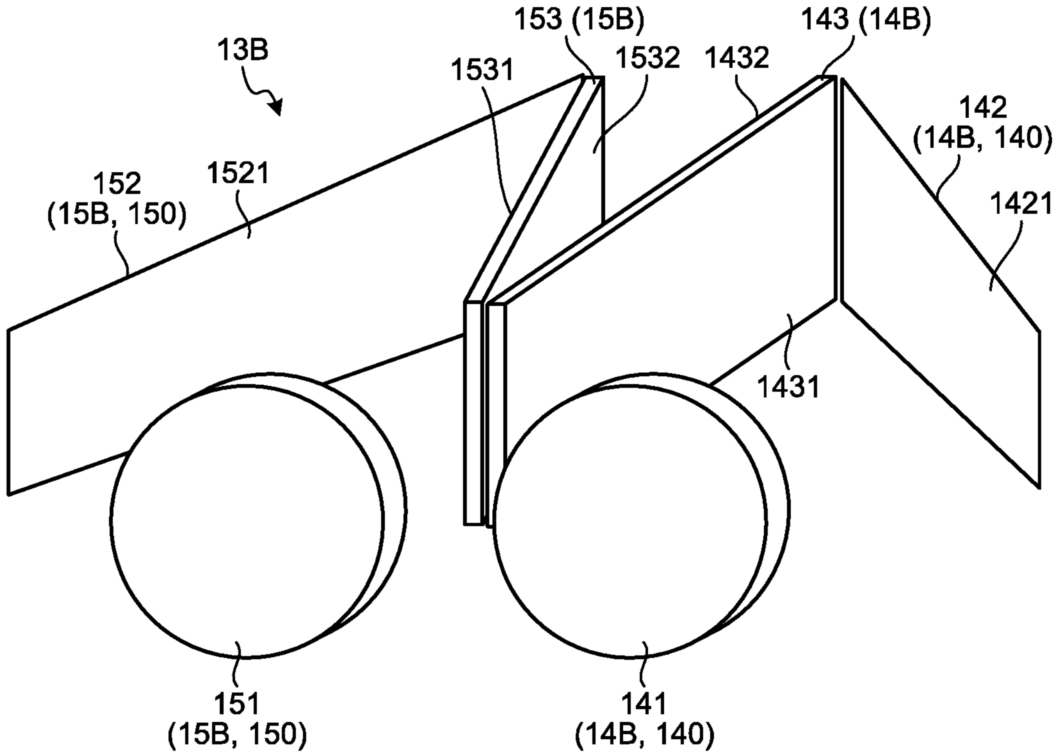
FIG. 15A is a diagram depicting a configuration of a medical imaging device according to a third embodiment.
Figure 15B:
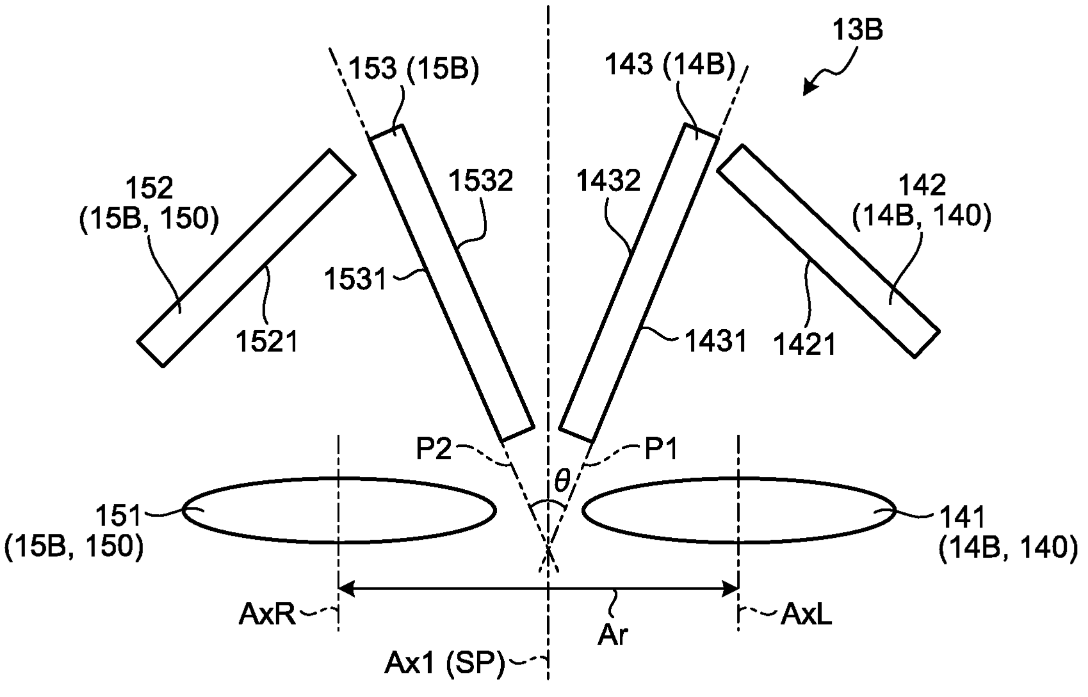
FIG. 15B is a diagram depicting a configuration of the medical imaging device according to the third embodiment.

FIG. 15A and FIG. 15B are diagrams depicting a configuration of a medical imaging device 13B according to the third embodiment. Specifically, FIG. 15A is a diagram corresponding to FIG. 10A, and is a perspective view of the medical imaging device 13B as viewed from a distal end side thereof. FIG. 15B is a diagram corresponding to FIG. 10B, and is a diagram of the medical imaging device 13B as viewed from thereabove in FIG. 15A.

In the medical imaging device 13B according to this third embodiment, as depicted in FIG. 15A or FIG. 15B, an arrangement posture of left and right eye mirrors 142 and 152 and left and right eye imaging elements 143 and 153 are different from those in the medical imaging device 13 (FIG. 10A and FIG. 10B) described above with respect to the second embodiment.

Specifically, as depicted in FIG. 15A or FIG. 15B, the left and right eye imaging elements 143 and 153 according to this third embodiment are arranged in a posture where proximal end sides thereof are separated by a predetermined interval, in contrast to the left and right eye imaging elements 143 and 153 (FIG. 10A and FIG. 10B) described above with respect to the second embodiment. That is, the left and right eye imaging elements 143 and 153 according to this third embodiment are arranged such that, as depicted in FIG. 10B, an angle θ formed between a plane P1 including a left eye light receiving surface 1431 and a plane P2 including a right eye light receiving surface 1531 is an acute angle.

Further, inclination angles of the left and right eye mirrors 142 and 152 according to this third embodiment with respect to a central axis Ax1 of the left and right eye reflecting surfaces 1421 and 1521 have been changed, as depicted in FIG. 15A or FIG. 15B, from the left and right eye mirrors 142 and 152 (FIG. 10A and FIG. 10B) described above with respect to the second embodiment, correspondingly to the above described arrangement posture of the left and right eye imaging elements 143 and 153.

Even when the arrangement postures of the left and right eye mirrors 142 and 152 and the left and right eye imaging elements 143 and 153 are changed as described above, a left eye imaging unit 14B (a left eye objective lens 141, the left eye mirror 142, and the left eye imaging element 143) and a right eye imaging unit 15B (a right eye objective lens 151, the right eye mirror 152, and the right eye imaging element 153) are arranged symmetrically to each other with reference to a plane SP. Further, the left and right eye imaging elements 143 and 153 are arranged such that the left and right eye light receiving surfaces 1431 and 1531 are respectively positioned on the planes P1 and P2 different from each other, and the reverse surfaces 1432 and 1532 oppose each other with respect to an optical axis juxtaposition direction Ar.

The above described medical imaging device 13B according to this third embodiment provides, in addition to effects similar to those of the above described second embodiment, the following effect.

In the medical imaging device 13B according to this third embodiment, the left and right eye imaging elements 143 and 153 are arranged such that the plane P1 including the left eye light receiving surface 1431 and the plane P2 including the right eye light receiving surface 1531 intersect each other at an acute angle.

Therefore, a gap is able to be provided between the reverse surfaces 1432 and 1532 of the left and right eye imaging elements 143 and 153, and various members, such as the above described signal processing unit and the like, are able to be installed in this gap.

Other Embodiments

Thus far, modes for carrying out the present disclosure have been described, but the present disclosure is not to be limited to the above described first to third embodiments only.

In the above described first embodiment, a medical imaging device according to the present disclosure is formed as the endoscope camera head 4, but the first embodiment is not limited to this formation.

For example, in a rigid endoscope or a flexible endoscope, a medical imaging device according to the present disclosure may be provided at a distal end of an insertion tube to be inserted into a living body. Further, a medical imaging device according to the present disclosure may be provided in a microscopic unit of a medical observation device that executes imaging by enlargement of a predetermined field area inside a subject (inside a living body) or on a surface of the subject (on a surface of the living body) (for example, see Japanese Unexamined Patent Application, Publication No. 2016-42981). Furthermore, a medical imaging device according to the present disclosure may be provided in a capsule type endoscope.

In the above described first embodiment, a twin lens relay type scope is adopted as the scope 2, but the first embodiment is not limited to this adoption. For example, instead of the scope 2, a single lens scope of the single lens pupil split type (for example, see Japanese Unexamined Patent Application, Publication No. 06-59199) may be adopted, which has an optical system arranged in a single optical path in the scope, takes in an observation light through the optical system, splits the observation light into two areas, and generates left and right eye observation lights having a parallax from each other.

In the above described first embodiment, as the scope 2, a squint eyed type scope may be adopted, which has a field in front thereof and diagonal to the central axis of the scope 2.

In the above described first embodiment, the left and right eye imaging elements 472 and 482 are arranged such that the left and right eye light receiving surfaces 472A and 482A are positioned on the same plane, but the first embodiment is not limited to this arrangement. For example, the left and right eye light receiving surfaces 472A and 482A may be configured to be arranged to come off from the same plane, and to be inclined at a predetermined angle so as to oppose each other.

In the above described second and third embodiments, the medical imaging devices 13 and 13B are provided in the scope 81 that is a rigid endoscope, but the second and third embodiments are not limited to this provision.

For example, the medical imaging device 13 or 13B may be provided in a rigid endoscope that does not have the bent portion 812. Further, the scope 81 may be a flexible endoscope, and the medical imaging device 13 or 13B may be provided in the flexible endoscope. Furthermore, the medical imaging device 13 or 13B may be provided in a camera head, which is attachably and detachably provided in the above described twin lens scope of the twin lens relay type described with respect to the first embodiment or a single lens scope of the single lens pupil split type, and which images left and right eye observation lights taken in by the scope. Moreover, the medical imaging device 13 or 13B may be provided in a microscopic unit of a medical observation device that executes imaging by enlargement of a predetermined field area inside a subject (inside a living body) or on a surface of the subject (on a surface of the living body). In addition, the medical imaging device 13 or 13B may be provided in a capsule type endoscope.

In the above described second and third embodiments, the left and right eye imaging elements 143 and 153 are respectively formed of imaging elements having the rectangular shaped left and right eye light receiving surfaces 1431 and 1531, but these embodiments are not limited to this formation, and similarly to the left and right eye mirrors 142 and 152, each of the left and right eye light receiving surfaces 1431 and 1531 may be formed to have a trapezoidal shape.

In the above described second and third embodiments, the left and right eye mirrors 142 and 152 may be changed to, for example, prisms or the like, as long as the prisms have the left and right eye reflecting surfaces 1421 and 1521.

In a medical imaging device according to the present disclosure, left and right eye imaging elements are arranged such that short sides of each of left and right eye light receiving surfaces are along a direction, in which optical axes of left and right eye observation lights are juxtaposed, and long sides thereof oppose each other. In other words, the left and right eye imaging elements are arranged such that the long sides of the left and right eye light receiving surfaces are juxtaposed in parallel with each other in the direction, in which the optical axes of the left and right eye observation lights are juxtaposed.

Therefore, the medical imaging device according to the present disclosure provides an effect of enabling downsizing by decrease in size thereof in the direction, in which the optical axes of the left and right eye observation lights are juxtaposed.

Further, a medical observation system according to the present disclosure provides an effect similar to that of the above described medical imaging device, since the medical observation system includes the above described medical imaging device.

Although the disclosure has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. A medical imaging device, comprising:

a left eye imaging element including a left eye light receiving surface configured to receive left eye observation light from an observed region of a subject, the left eye light receiving surface being rectangular, and the left eye imaging element being configured to output a left eye image signal corresponding to the left eye observation light; and a right eye imaging element including a right eye light receiving surface configured to receive right eye observation light being an observation light from the observed region and having a parallax from the left eye observation light, the right eye light receiving surface being rectangular, and the right eye imaging element being configured to output a right eye image signal corresponding to the right eye observation light, wherein the left eye imaging element and the right eye imaging element are arranged such that:

each of short sides of the left eye light receiving surface and short sides of the right eye light receiving surface are along a direction in which an optical axis of the left eye observation light and an optical axis of the right eye observation light are juxtaposed with each other; and a long side of the left eye light receiving surface and a long side of the right eye light receiving surface oppose each other.

2. The medical imaging device according to claim 1, further comprising:

a left eye imaging optical system configured to form an image of the left eye observation light having a circular cross section, on the left eye light receiving surface; and a right eye imaging optical system configured to form an image of the right eye observation light having a circular cross section, on the right eye light receiving surface.

3. The medical imaging device according to claim 1, wherein the medical imaging device is an endoscope camera head.

4. A medical observation system, comprising:

the medical imaging device according to claim 1;

a control device configured to process the left eye image signal and the right eye image signal output from the medical imaging device, and generate a three dimensional image signal; and a display device configured to display thereon a stereoscopic image based on the three dimensional image signal generated by the control device.

5. The medical observation system according to claim 4, wherein scanning lines of the left eye imaging element and right eye imaging element are respectively along a long side direction of the left eye light receiving surface and a long side direction of the right eye light receiving surface, and the control device includes an image signal generating unit configured to respectively process the left eye image signal and the right eye image signal, and respectively execute rotation correction on a left eye image based on the left eye image signal and a right eye image based on the right eye image signal.

6. The medical observation system according to claim 4, wherein the left eye imaging element and the right eye imaging element are arranged such that each of horizontal scanning directions and vertical scanning directions thereof are in the same direction.

7. The medical imaging device according to claim 1, wherein the short sides of the left eye light receiving surface and the short sides of the right eye light receiving surface are parallel to a central axis of the medical imaging device.

* * * * *